United States Patent [19]

Nomura et al.

[11] Patent Number: 5,422,031
[45] Date of Patent: Jun. 6, 1995

[54] HAIR TINTING SHAMPOO

[75] Inventors: Tadashi Nomura, Frankfurt; Satoshi Onitsuka, Darmstadt, both of Germany

[73] Assignee: Kao Corporation, Tokyo, Japan

[21] Appl. No.: 135,656

[22] Filed: Oct. 14, 1993

Related U.S. Application Data

[63] Continuation of Ser. No. 942,226, Sep. 9, 1992, abandoned.

[30] Foreign Application Priority Data

Sep. 9, 1991 [DE] Germany .................. 41 29 926.4

[51] Int. Cl.⁶ .................. C11D 1/12; C11D 1/755; A61K 7/13
[52] U.S. Cl. .................. 252/174.17; 252/547; 252/552; 252/556; 252/559; 252/DIG. 13; 8/435; 8/525
[58] Field of Search .................. 252/174.17, 174.11, 252/171, 547, 551, 552, 555, 556, 559, DIG. 1, DIG. 13; 424/70; 8/435

[56] References Cited

U.S. PATENT DOCUMENTS

| | | | |
|---|---|---|---|
| 4,154,706 | 5/1979 | Kenkare et al. | 252/DIG. 13 |
| 4,857,070 | 8/1989 | Seidel et al. | 8/408 |
| 4,923,977 | 5/1990 | Lang et al. | 536/20 |
| 4,959,206 | 9/1990 | Noguera et al. | 252/DIG. 13 |
| 4,976,952 | 12/1990 | Lang et al. | 424/47 |
| 5,015,414 | 5/1991 | Kamegai et al. | 252/DIG. 13 |
| 5,025,069 | 6/1991 | Deguchi et al. | 252/DIG. 13 |
| 5,078,990 | 1/1992 | Martin et al. | 252/DIG. 13 |
| 5,084,212 | 1/1992 | Farris et al. | 252/DIG. 14 |
| 5,089,257 | 2/1992 | Schrader et al. | 424/70 |
| 5,100,573 | 3/1992 | Bolzer | 252/DIG. 13 |
| 5,109,127 | 4/1992 | Sekiguchi et al. | 252/174.17 |
| 5,137,715 | 8/1992 | Hoshowski et al. | 252/DIG. 13 |
| 5,145,607 | 9/1992 | Rich | 252/DIG. 13 |
| 5,151,209 | 9/1992 | McCall et al. | 252/DIG. 13 |
| 5,151,210 | 9/1992 | Steuri et al. | 252/DIG. 13 |
| 5,154,850 | 10/1992 | Deguchi et al. | 252/DIG. 13 |

FOREIGN PATENT DOCUMENTS

| | | |
|---|---|---|
| 0070074 | 1/1983 | European Pat. Off. . |
| 0137178 | 4/1985 | European Pat. Off. . |
| 0367926 | 5/1990 | European Pat. Off. . |
| 2034295 | 2/1971 | Germany . |

*Primary Examiner*—Christine Skane
*Assistant Examiner*—Patricia L. Hailey
*Attorney, Agent, or Firm*—Birch Stewart Kolasch & Birch

[57] ABSTRACT

A tinting shampoo with an efficient and gentle cleansing effect and improved color absorption which contains at least one direct dyestuff in a water-based surfactant mixture comprising at least an anion-active surfactant in a proportion of about 5 to 35% by weight, especially a mixture of sulphosuccinate and a lauroyl sarcosinate, 0.5 to 10% by weight of a surface-active amine oxide, and about 2.5 to about 15% by weight of an alkyl polyglycoside, and, optionally, about 0.5 to about 10% by weight of an amphoteric surfactant and (or) about 0.5 to about 5% by weight of a further non-ionic surfactant.

14 Claims, No Drawings

HAIR TINTING SHAMPOO

This application is a continuation of application Ser. No. 07/942,266, filed on Sep. 9, 1992, now abandoned.

The present invention refers to a coloring shampoo which not only provides thorough and gentle cleansing of the hair, but also shows an excellent tinting effect. Shampoos with coloring properties, so-called tinting shampoos, have been known for a long time. Normally, they consist of a surfactant base and one or more direct dyes included therein. Examples of those tinting shampoos may be found in cosmetic monographies, e.g. K. Schrader, Grundlagen und Rezepturen der Kosmetika, 2nd Ed. (Huethig Buchverlag Heidelberg, 1989), pp.805 to 806, and p.814.

These coloring shampoos suffer from the disadvantage that hair colorations achieved by them are often not sufficiently intense and, therefore, fade or even disappear completely after relatively few shampoo treatments.

Hence the invention starts from the problem of creating a composition for a coloring shampoo that does not show these disadvantages, i.e. that not only cleanses the hair thoroughly and gently, but also allows the direct dyestuff to be absorbed in such a way as to achieve an improved and lasting color intensity.

The present inventors have found that the solution to this problem is the use of a coloring shampoo comprising at least one direct hair dyestuff which is present in a surfactant mixture in an aqueous base, whereby the base contains a surfactant mixture of the following composition:

5 to 35% by weight of an anionic surfactant;
0.5 to 10% by weight of a surface-active amine oxide;
2.5 to 15% by weight of an alkyl polyglycoside of the general formula RO $(R^1O)_t Z_x$, where Z represents a reducing saccharide residue with 5 to 6 carbon atoms, R represents an alkyl having group from 8 to 18 carbon atoms, $R^1$ represents an ethylene or propylene residue, t is a number from zero to ten and x a number from one to five, and, optionally, 0.5 to 5% by weight of another nonionic surfactant, and (or) about 0.5 to 10% by weight of an amphoteric surfactant.

The above percentages each refer to the total composition of the tinting shampoo.

EP-A 137 178 already discloses coloring shampoos containing, in addition to a direct dyestuff, an anionic surfactant and an "auxiliary surfactant" which should be a cationic and/or a betaine surfactant.

However, these compositions, too, are not entirely satisfactory with respect to optimal color luster and color depth imparted to the hair.

Another problem has been set in EP-A 367 926, again describing hair dyeing or hair tinting products on the basis of at least one direct dyestuff in a base mixture of surfactants and usual additives, whereby this base mixture contains 2.5 to 20% by weight of at least one amphoteric surfactant,
1 to 10% by weight of at least one surface active amine oxide, and
1 to 10% by weight of at least one non-ionic surfactant.

It is not possible to draw any conclusions as to a solution to the problem of the present invention from the publication mentioned above, especially because this publication clearly states that anionic surfactants, particularly fatty alcohol ether sulphates, should only be used in minor quantities, if at all.

Finally, from EP-A 46 543, preparations are known which simultaneously color, wash, and condition the hair. However, these products obligatorily include oxidation dyes, as compared to the present invention which is primarily related to direct dyestuffs. In addition, the shampoo basis composition used in this European publication is fundamentally different in its surfactant composition from the surfactant composition used in the present invention.

Anionic surfactants suitable within the scope of the present invention are especially alkali salts of sulphosuccinic acid semi-esters, and particularly the disodium salt of the monooctylsulphosuccinate and alkali salts of long-chain monoalkyl ethoxy sulphosuccinates.

An additionally preferred category of anionic surfactants are long-chain acyl sarcosinates or their alkali salts, e.g. sodium lauroylsarcosinate.

As already mentioned, the proportion of anionic surfactants in the compositions of the invention is about 5 to about 35% by weight, based on the total composition of the coloring shampoo. A preferred range thereby is about 8 to about 25, and preferably 10 to 20% by weight of anion-active surfactant. A preferred surfactant mixture is composed of an alkali salt of a sulphosuccinate, e.g. disodium laurylether sulphosuccinate, and an acylamino carboxylic acid salt, e.g. sodium lauroyl sarcosinate, preferably in a weight proportion of about 5:1 to 2:1, and particularly 3 to 4:1. In the place of or as a supplement to the preferably used anionic surfactants, as mentioned above, further anion-active surfactants may be used, e.g. the known $C_{10}$–$C_{18}$ alkylether sulphates, especially the $C_{12}$–$C_{14}$ alkylether sulphates or laurylether sulphate, particularly those containing one to four ethylene oxide groups per mole.

Further suitable anion-active surfactants are fatty alcohol sulphates, e.g. laurylsulphate, monoglyceride sulphates, fatty acid amide sulphates produced by ethoxylation and following sulphation of fatty acid monoalkanolamides, alkylether carboxylic acids and alkali salts of long-chain alkylphosphates which are also mild and especially skin-compatible detergents.

In admixture with other anionic surfactants, well-known protein-fatty acid-condensation products may also be used. A survey of anion-active surfactants employed in shampoos is, e.g., given in the monography of K. Schrader, l.c., pp.683 to 691.

A further component of the composition of the present invention is a surface-active oxide in a proportion of about 0.5 to about 10% by weight, preferably 1 to 5, and particularly 1.5 to 3% by weight of the total composition. Suitable amine oxides are e.g. $C_{12}$–$C_{18}$ alkyl dimethyl amine oxides, e.g. lauryl dimethyl amine oxide or coco-di(hydroxyethyl)amine oxide.

The long-chain alkyl residue may also be substituted by amide groups, such as a $C_7$–$C_{17}$ alkanoylamino-3-dimethyl amino propane-3-N-oxide. Polyoxyethylated amine oxides, are also suitable, as are amine oxides of the type diethylaminopropyl palmitamide-N-oxide, etc.

Finally, the compositions of the present invention comprise 2.5 to 15% by weight of an alkylpolyglycoside of the general formula $RO(R^1O)_t Z_x$, where Z represents a reducing saccharide residue with 5 to 6 carbon atoms, R an alkyl group from 8 to 18 carbon atoms, $R^1$ an ethylene or propylene residue, t a number between zero and ten and x a number between one and five. The preferred proportion is between 5 and 10% by weight of the total composition. Mixtures of anion-active surfactants and alkylpolyglycosides and their use in hair shampoos are already common knowledge, e.g. from EP-A 70 074.

The alkyl polyglycosides described therein are principally suitable as well within the scope of the present invention; however, this invention uses, as a specially preferred alkyl polyglycoside, a material with approximately 9 to 11 carbon atoms in the alkyl chain and a condensation degree of less than 1.4, preferably 1.35.

Mixtures of sulphosuccinates with alkyl polyglycosides are already known as well from EP-A 358 216; the mixtures described therein are also excellently suitable for use in the compositions of the present invention.

In a preferred embodiment, the compositions of this invention also contain 0.5 to 10, preferably 1 to 5% by weight calculated based on the total composition, of one or more amphoteric surfactants. The various known betaines like fatty acid amido alkylbetaines, long-chain alkyl aminopropionates as well as preferably sulphobetaines are suitable as such. A particularly suitable betaine in this respect is laurylhydroxysulphobetaine.

Schrader, l.c., pp. 598 to 600, also describes amphoteric surfactants suitable for shampoos.

Preferred optional ingredients of the composition of this invention are additional nonionic surfactants, preferably in a proportion of approximately 0.5 to approximately 5.0%, especially 1 to 3% by weight calculated based on the total composition.

Such nonionic surfactants are, e.g., the various sorbitol esters, for example, polyethylene glycol sorbitan stearic acid ester such as polyoxyethylene sorbitan monostearate with 20 to 60 ethylene oxide units, fatty acid polyglycolesters or fatty acid glyceride oxyethylate, fatty alcohol polyglycolether and also mixed condensates from ethylene oxide and propylene oxide, as they are, e.g., available under the trade name "Pluronic".

As additional nonionic surfactant ingredients, the coloring shampoos of the invention may contain, e.g., long-chain fatty acid monoalkanolamides and dialkanolamides, for example, coconut fatty acid monoethanolamide or myristic fatty acid diethanolamide. The proportion of these alkanolamides is preferably between about 0.2 and 2.5, especially 0.5 and 2% by weight of the total composition.

Such mixtures of alkylpolyglycosides with fatty acid alkanolamides are, e.g. the object of EP-A 70 076.

Hair coloring shampoos of this invention may, of course, include all other substances which are usually employed in those products. As such shall be mentioned: complexing agents, further dyestuffs to tint the shampoo itself, preservatives, pH regulators, viscosity regulators such as inorganic salts, as far as they are not part of the surfactant composition, fragrances, agents to give pearly luster, thickeners, etc. A list of those additional substances is, e.g., disclosed by Schrader, l.c., pp.695 to 722.

Additional useful additives are hair conditioning substances. As such particularly cationic polymers are used, preferably in a proportion between 0.1 to 1.5, especially 0.25 to 1.0% by weight of the total composition. From EP-A 337 354, the use of cationic polymers in alkylpolysaccharide surfactant preparations is already known; the cationic polymers listed therein on pp.3 to 7 are also suitable as conditioning additives in the compositions of this invention.

Additional hair conditioning additives are the well-known protein hydrolyzates, e.g. in a proportion of 0.25 to 5% by weight, preferably 0.5 to 2.5% by weight of the total composition. Moreover, water-soluble collagen or water-soluble collagen derivatives are suitable. Finally, as already known, the various polysiloxanes may also be used additionally as conditioning agents in the hair coloring shampoo of this invention. The preferred proportion thereof is between approximately 0.5 and approximately 7.5, especially 1 to 5% by weight of the total composition. Suitable are high volatile as well as less volatile cyclic or linear polysiloxanes, e.g. silicone oils known by their common names "dimethicone" or "phenyldimethicone" and (or) "cyclomethicone".

Naturally, an essential part of the hair coloring shampoos of the invention are direct dyestuffs. Their selection and concentration, of course, is dependent on the desired color shade, because of which the following list may only be taken as an example:

Especially suitable are the so-called "Arianor" dyestuffs such as

| Basic Brown 17, | Colour Index No. 12,251; |
|---|---|
| Basic Brown 16, | C.I. No. 12,250; |
| Basic Red 76, | C.I. No. 12,245; |
| Basic Yellow 57, | C.I. No. 12,719; |
| Basic Blue 99, | C.I. No. 56,059; |
| Basic Violet, | C.I. No. 45,170 or |
| Basic Violet 1, | C.I. No. 42,535 and |
| Basic Violet 3, | C.I. No. 42,555; |
| Acid Yellow 1, | C.I. No. 10,316; |
| Acid Yellow 9, | C.I. No. 13,015; |
| Disperse Yellow 3, | C.I. No. 11,855; and |
| Disperse Yellow 1, | C.I. No. 10,345. |

Direct hair dyes are also listed at Schrader, l.c., pp. 800 to 805. Of course natural direct dyestuffs, such as henna, may be used additionally.

The following examples give non-limiting illustrations of the invention:

EXAMPLE 1

| Disodium laurylether sulphosuccinate (30%) | 27.00% (by weight) |
|---|---|
| Sodium lauroylsarcosinate (30%) | 7.50 |
| $C_9$–$C_{11}$-Alkyl polyglycoside (x = 1.35), 30% | 19.00 |
| Dimethyl laurylamine oxide (35%) | 6.00 |
| Lauryl hydroxy sulphobetaine (30%) | 3.50 |
| PEG-160-sorbitan tristearate | 1.00 |
| Polysorbate 40 | 1.00 |
| Preservatives (parabens) | 0.30 |
| Complexing agents (EDTA) | 0.30 |
| Cationic polymer (polydimethyl diallyl ammonium chloride) | 0.50 |
| Citric acid | 1.00 |
| Henna extract | 0.10 |
| Basic Yellow 57 | 0.01 |
| Basic Red 76 | 0.08 |
| Basic Blue 99 | 0.01 |
| Water | ad 100.00 |

The application of this coloring shampoo produces a significant, lasting red shade on the hair.

Example 2

| Disodium laurylether sulphosuccinate (2 to 4 EO-units; 30%) | 25.00% (by weight) |
|---|---|
| $C_9$–$C_{11}$-Alkylpolyglycoside (x = 1.35), | 20.00 |

| -continued | |
|---|---|
| 35% | |
| Lauryl dimethyl amine oxide (35%) | 4.50 |
| Coconut fatty acid amido propylbetaine (35%) | 3.50 |
| Coconut fatty acid protein-condensate, sodium salt (30%) | 2.00 |
| Complexing agent (HEDP) | 0.50 |
| Opacifier | 2.00 |
| Solubilizer (polyoxyethylated hydrated castor oil fatty acid ester) | 1.00 |
| Cationic cellulose derivative (Polyquaternium-10) | 0.50 |
| Dyestuff C.I. No. 12,719 | 0.02 |
| Dyestuff C.I. No. 12,251 | 0.02 |
| Dyestuff C.I. No. 12,250 | 0.04 |
| Dyestuff C.I. No. 56,059 | 0.03 |
| Perfume | 0.65 |
| Preservatives (parabens) | 0.25 |
| Water | ad 100.00 |

After washing the hair with this coloring shampoo, a bright light blonde tone is achieved.

We claim:

1. A hair tinting shampoo comprising at least one direct dyestuff in a water based surfactant mixture, wherein said surfactant mixture comprises
   a) 5 to 35% by weight of at least one anionic surfactant;
   b) 0.5 to 10% by weight of a surface-active amine oxide;
   c) 2.5 to 15% by weight of an alkyl polyglycoside of the formula $RO(R^1O)_tZ_x$,
wherein Z denotes a reducing saccharide residue containing 5 to 6 carbon atoms, R denotes an alkyl group containing 8 to 18 carbon atoms, $R^1$ denotes an ethylene or propylene residue, t denotes a number between zero and 10 and x denotes a number between one and five.

2. The hair tinting shampoo according to claim 1, wherein said anionic surfactant comprises a mixture of 8 to 20% by weight, calculated based on the total composition, of an alkali salt of a sulphosuccinic acid semiester and an alkali salt of a $N-C_{12}-C_{18}$ acylsarcosinate in a proportion of 2:1 to 5:1 by weight.

3. The hair tinting shampoo according to one of claims 1 or 2, wherein said alkyl polyglycoside comprises a $C_9-C_{11}$ alkyl polyglycoside having a condensation degree (x) of less than 1.4.

4. The hair tinting shampoo according to one of claims 1 or 2, further comprising an amphoteric surfactant in a proportion of 0.5 to 10% by weight, calculated based on the total composition.

5. The hair tinting shampoo according to claim 4, comprising 1.5 to 5% by weight of lauryl hydroxy sulphobentaine.

6. The hair tinting shampoo according to claims 1 or 2, further comprising an additional non-ionic surfactant in a proportion of 0.5 to 5% by weight of the total composition.

7. The hair tinting shampoo according to claim 6, wherein said additional non-ionic surfactant is a polyoxyethylene sorbitan monoester in a proportion of 1 to 2.5% weight, calculated based on the total composition.

8. A method for tinting human hair, comprising applying to the hair the hair tinting shampoo composition according to claim 1, and rinsing said hair tinting shampoo composition from the hair to obtain tinted hair.

9. The method for tinting human hair according to claim 8, wherein said anionic surfactant of said hair tinting shampoo composition comprises a mixture of 8 to 20% by weight, calculated based on the total composition, of an alkali salt of a sulphosuccinic acid semiester and an alkali salt of a $N-C_{12}-C_{18}$ acylsarcosinate in a proportion of 2:1 to 5:1 by weight.

10. The method for tinting human hair according to claim 8, wherein said alkylpolyglycoside comprises a $C_9-C_{11}$ alkyl polyglycoside having a condensation degree (x) of less than 1.4.

11. The method for tinting human hair according to claim 8, wherein said hair tinting shampoo composition further comprises an amphoteric surfactant in a proportion of 0.5 to 10% by weight, calculated based on the total composition.

12. The method for tinting human hair according to claim 11, wherein said amphoteric surfactant is lauryl hydroxy sulphobetaine, and is present in a proportion of 1.5 to 5% by weight, calculated based on the total composition.

13. The method for tinting human hair according to claim 8, wherein said hair tinting shampoo composition further comprises an additional non-ionic surfactant in a proportion of 0.5 to 5% by weight based on the total composition.

14. The method for tinting human hair according to claim 13, wherein said additional non-ionic surfactant is polyoxyethylene sorbitan monoester in a proportion of 1 to 2.5% by weight, calculated based on the total composition.

* * * * *